US011304896B2

(12) United States Patent
Crowe-White (10) Patent No.: US 11,304,896 B2
(45) Date of Patent: Apr. 19, 2022

(54) ANTIOXIDANT INFUSED GUM FOR IMPROVING ORAL HEALTH

(71) Applicant: THE BOARD OF TRUSTEES OF THE UNIVERSITY OF ALABAMA, Tuscaloosa, AL (US)

(72) Inventor: Kristi Crowe-White, Tuscaloosa, AL (US)

(73) Assignee: THE BOARD OF TRUSTEES OF THE UNIVERSITY OF ALABAMA, Tuscaloosa, AL (US)

( * ) Notice: Subject to any disclaimer, the term of this patent is extended or adjusted under 35 U.S.C. 154(b) by 65 days.

(21) Appl. No.: 16/527,908

(22) Filed: Jul. 31, 2019

(65) Prior Publication Data
US 2020/0038319 A1    Feb. 6, 2020

Related U.S. Application Data

(60) Provisional application No. 62/712,353, filed on Jul. 31, 2018.

(51) Int. Cl.
| | | |
|---|---|---|
| *A61K 9/68* | (2006.01) |
| *A61K 36/537* | (2006.01) |
| *A61K 36/54* | (2006.01) |
| *A61K 36/534* | (2006.01) |
| *A61K 36/82* | (2006.01) |
| *A61K 36/8962* | (2006.01) |
| *A61K 8/67* | (2006.01) |
| *A61K 36/66* | (2006.01) |
| *A61K 36/752* | (2006.01) |
| *A61K 36/9066* | (2006.01) |
| *A61Q 11/00* | (2006.01) |
| *A23L 27/10* | (2016.01) |
| *A23L 33/135* | (2016.01) |
| *A61K 36/9068* | (2006.01) |

(52) U.S. Cl.
CPC ............ *A61K 9/0058* (2013.01); *A23L 27/10* (2016.08); *A23L 33/135* (2016.08); *A61K 8/67* (2013.01); *A61K 36/534* (2013.01); *A61K 36/537* (2013.01); *A61K 36/54* (2013.01); *A61K 36/66* (2013.01); *A61K 36/752* (2013.01); *A61K 36/82* (2013.01); *A61K 36/8962* (2013.01); *A61K 36/9066* (2013.01); *A61K 36/9068* (2013.01); *A61Q 11/00* (2013.01)

(58) Field of Classification Search
CPC .............. A61K 9/68; A23G 4/00; A23L 1/236
USPC ..................................... 426/3, 548; 424/48
See application file for complete search history.

(56) References Cited

U.S. PATENT DOCUMENTS

| 4,148,872 A | * | 4/1979 | Wagenknecht | ........ A61K 8/375 424/48 |
| 2015/0264958 A1 | * | 9/2015 | Kabse | ..................... A23G 4/10 426/5 |
| 2016/0346171 A1 | * | 12/2016 | Abe | ........................ A23G 3/48 |

OTHER PUBLICATIONS

Chakraborty et al., "Artifical sweeteners—a review." J Food Sci Technol (Apr. 2014) 51(4):611-621. (Year: 2014).*
Robert Morello, "Howe to Grind Cinnamon Sticks." www.leaf.tv; published online Jul. 8, 2014 (Year: 2014).*
Tonetti, Maurizio S., and Thomas E. Van Dyke. Periodontitis and atherosclerotic cardiovascular disease: consensus report of the Joint EFP/AAPWorkshop on Periodontitis and Systemic Diseases. Journal of Periodontology. 2013;84(4S):S24-S29.
Shan B, Cai YZ, Sun M, Corke H. Antioxidant Capacity of 26 Spice Extracts and Characterization of Their Phenolic Constituents. Journal of Agricultural and Food Chemistry. 2005;53(20):7749-7759.
Ock Kyoung Chun, et al., Daily consumption of phenolics and total antioxidant capacity from fruit and vegetables in the American diet. Journal of the Science of Food and Agriculture. 2005;85(10):1715-1724.
Ginsburg I, Koren E, Shalish M, Kanner J, Kohen R. Saliva increases the availability of lipophilic polyphenols as antioxidants and enhances their retention in the oral cavity. Archives of Oral Biology. 2012;57(10):1327-1334.
GRN No. 400 D-psicose. 2018; https://www.accessdata.fda.gov/scripts/fdcc/index.cfm?set=GRASNotices&id=400 Accessed May 12, 2018.
Suna S, Yamaguchi F, Kimura S, Tokuda M, Jitsunari F. Preventive effect of d-psicose, one of rare ketohexoses, on di-(2-ethylhexyl) phthalate (DEHP)-induced testicular injury in rat. Toxicology Letters. 2007;173(2):107-117.
Hossain A, Yamaguchi F, Hirose K, et al. Rare sugar d-psicose prevents progression and development of diabetes in T2DM model Otsuka Long-Evans Tokushima Fatty rats. Drug Design, Development and Therapy. 2015;9:525-535.
Prior RL, Hoang H, Gu L, et al. Assays for hydrophilic and lipophilic antioxidant capacity (oxygen radical absorbance capacity (ORAC(FL))) of plasma and other biological and food samples. J Agric Food Chem. 2003;51(11):3273-3279.

(Continued)

*Primary Examiner* — Walter E Webb
(74) *Attorney, Agent, or Firm* — Meunier Carlin & Curfman LLC (57) ABSTRACT

Disclosed herein are compositions and methods for treating, reducing or preventing oxidative stress in a subject. The compositions can be chewable confectionaries comprising a chewable base, one or more unprocessed phytochemical ingredients, and a sweetener comprising allulose. The unprocessed phytochemical ingredients can include ground plant materials selected from cinnamon, nutmeg, allspice, or combinations thereof. The chewable confectionary can exhibit a polyphenolic content of at least 100 μg gallic acid equivalents (GAE) or greater, per gram of the chewable confectionary and an antioxidant capacity of at least 3,200 μM Trolox equivalents per gram of the chewable confectionary, as determined by the oxygen radical absorbance (ORAC) assay. Kits, methods of making and using the chewable confectionary are also disclosed.

22 Claims, 3 Drawing Sheets

(56) References Cited

OTHER PUBLICATIONS

Hoff, JE, et al., A method for determination of tannins in foods by means of immobilized protein. Journal of Food Science. 1977;42(6):1566-1569.

Siebert, KJ, et al., An alternate mechanism for the astringent sensation of acids. Food Quality and Preference. 2003;15:13-18.

Bamidele, O., Akinnuga, A. M., Alagbonsi, I. A., Ojo, O. A., Olorunfemi, J. O. and Akuyoma, M. A. 2011. Effects of ethanolic extract of *Myristica fragrans* Houtt. (nutmeg) on some heamatological in albino rats. International Journal of Medicine and Medical Sciences 3 (6): 215-218.

Somani, R., Karve, S., Jain, D., Jain, K. and Singhai, A. K. 2008. Phytochemical and pharmacological potential of Myristica fragrans Houtt: A comprehensive review. Pharmacognosy Reviews 2 (3): 68-76.

\* cited by examiner

ANTIOXIDANT INFUSED GUM FOR IMPROVING ORAL HEALTH

CROSS-REFERENCE TO RELATED APPLICATIONS

This application claims the benefit of and priority to U.S. Provisional Application Ser. No. 62/712,353 filed on Jul. 31, 2018, the disclosure of which is expressly incorporated herein by reference in its entirety.

FIELD

The present disclosure generally relates to confectionary compositions, particularly to compositions for treating, reducing or preventing oral oxidative stress.

BACKGROUND

The role of the oral cavity in the pathogenesis of diseases of various systems such as the gastrointestinal tract, cardiovascular and immune systems has been established. While initially the oral cavity is considered to be mainly a source of various bacteria, their toxins and antigens, recent studies showed that it may also be a location and generator of oxidative stress. In the oral cavity, oxidative stress is associated with infection or inflammation of the gums (gingivitis) and other soft tissues (periodontitis). But oxidative stress in the oral cavity has been shown to be a major contributor to systemic oxidative stress—which can lead to chronic diseases, such as rheumatoid arthritis or vascular disease including heart attack or stroke.

Considering the number of diseases or conditions that result directly or indirectly from oral oxidative stress, few attempts have been made to attenuate oxidative stress in the oral environment. There is a need to provide compositions and methods to treat, reduce or prevent oral oxidative stress, and consequently conditions related to oral oxidative stress. The compositions and methods disclosed herein address these and other needs.

SUMMARY

In accordance with the purposes of the disclosed compositions and methods, as embodied and broadly described herein, the disclosed subject matter relates to compositions and to methods for treating, reducing or preventing oxidative stress in a subject. Accordingly, the compositions described herein exhibit antioxidant properties. For example, described herein are compositions comprising unprocessed phytochemical ingredients, such as an unprocessed plant material, wherein the phytochemical ingredients include naturally occurring phenolic compounds, preferably polyphenolic compounds. The compositions can be in the form of a chewable confectionary such as a chewing gum or a chewable tablet. In some examples, the chewable confectionary can include a chewable base, one or more unprocessed phytochemical ingredients (e.g., an unprocessed plant material), and a sweetener comprising allulose.

The unprocessed phytochemical ingredients present in the chewable confectionaries can be selected from *Cinnamomum* sp. (cinnamon), *Myristica fragrans* (nutmeg), *Pimenta dioica* (allspice), and combinations thereof. Other suitable unprocessed phytochemical ingredients that can be included in the chewable confectionary can include *Rosimarinus officinalis* (rosemary), *Ocium basilicum* (sweet basil), *Salvia officinalis* (sage), *Origanum valgare* (oregano), *Origanum marjoram* (marjoram), and *Mentha peperita* (mint), *Laurel nobilis* (bay leaves), *Petroselium crispum* (parsley), *Syzygium aromaticum* (clove), *Hyssopus officinalis* L. Var. *angustifolius* (hyssop), *Thymus vulgaris* L. (thyme), *Camellia sinensis* L. (tea), *Allium sativum* L. (garlic), *Zingiber officinale* (ginger), or *Curcuma longa* L. (turmeric). The unprocessed phytochemical ingredients described herein are not derived from a plant extract. In some embodiments, the unprocessed phytochemical ingredients can be ground plant material having an average particle size 0.4 mm or greater, preferably from 0.4 to 1.5 mm, more preferably from 0.6 to 1.0 mm.

The unprocessed phytochemical ingredients (or plant materials) can be present in an amount of 0.1% or greater by weight, preferably from 0.1% to 10% by weight, more preferably from 0.5% to 5% by weight, based on the total weight of the chewable confectionary. In some examples, the chewable confectionary can include cinnamon in an amount of 0.1% by weight or greater, preferably from 0.1% to 10% by weight, more preferably from 0.5% to 5% by weight, based on the weight of the chewable confectionary. In some embodiments, the chewable confectionary can include nutmeg in an amount of 0.1% by weight or greater, preferably from 0.1% to 10% by weight, more preferably from 0.5% to 5% by weight, based on the weight of the chewable confectionary. In some embodiments, the chewable confectionary can include allspice in an amount of 0.1% by weight or greater, preferably from 0.1% to 10% by weight, more preferably from 0.5% to 5% by weight, based on the weight of the chewable confectionary.

As described herein, the chewable confectionary also includes a sweetener comprising allulose. In some embodiments, the sweetener in the chewable confectionary consists essentially of allulose. The allulose can be present in an amount of 10% by weight or greater, preferably from 10% to 60% by weight, more preferably from 20% to 50% by weight, based on the weight of the chewable confectionary.

The chewable confectionary can further comprise a plasticizing agent, bulking agents, diluents, sweeteners, colorants, vitamins, prebiotics, probiotics, emulsifiers, and flavoring agents. In some embodiments, the chewable confectionary can comprise a controlled release agent, for regulating release of antioxidants from the chewable confectionary.

Kits comprising the chewable confectionaries are also disclosed herein. The kit can include at least three chewable confectionaries. In some examples, at least one of the chewable confectionary present in the kit is a chewing gum. The kit can further include directions for use and a suitable number of chewable confectionaries for a time determined for desired efficacy in reducing oxidative stress, such as at least two weeks or at least four weeks of consumption.

Methods of making and using the chewable confectionary are also disclosed. The method can include mixing a chewable base, one or more unprocessed phytochemical ingredients selected from *Cinnamomum* sp. (cinnamon), *Myristica fragrans* (nutmeg), and *Pimenta dioica* (allspice), and a sweetener comprising allulose.

As described herein, the chewable confectionary can be used to treat, reduce or prevent oral oxidative stress in a subject. In some embodiments, methods of using the chewable confectionary to treat, reduce or prevent oxidative stress include consuming the chewable confectionary comprising a therapeutically effective amount of antioxidants (from the unprocessed phytochemical ingredients and allulose) to treat, reduce or prevent oral oxidative stress in the subject.

In some examples, the chewable confectionary has a polyphenolic content of at least 100 μg gallic acid equivalents (GAE) or greater, preferably from 200 μg to 5 mg gallic acid equivalents (GAE) per gram of the chewable confectionary. In other examples, the chewable confectionary has an antioxidant capacity of at least 1,500 μM, preferably at least 2,500 μM, more preferably at least 10,000 μM Trolox equivalents per gram of the chewable confectionary, as determined by the oxygen radical absorbance (ORAC) assay. In further examples, the subject's saliva can exhibit an increase in total antioxidant capacity of at least 10% in Trolox equivalents per gram of the chewable confectionary after an oral residence time of greater than one minute, as determined by the oxygen radical absorbance (ORAC) assay, compared to the subject's saliva prior to chewing the chewable confectionary.

The chewable confectionary for treating oxidative stress is preferably consumed at least once per week, more preferably at least twice per week, most preferably daily. In some embodiments, the chewable confectionary can be consumed in combination with an additional therapeutic agent for treating, reducing or preventing oxidative stress.

Additional advantages of the disclosed process will be set forth in part in the description which follows, and in part will be obvious from the description, or can be learned by practice of the disclosed process. The advantages of the disclosed process will be realized and attained by means of the elements and combinations particularly pointed out in the appended claims. It is to be understood that both the foregoing general description and the following detailed description are exemplary and explanatory only and are not restrictive of the disclosed process, as claimed.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

The accompanying figures, which are incorporated in and constitute a part of this specification illustrate several aspects described below.

DETAILED DESCRIPTION

The materials, compounds, compositions, articles, and methods described herein can be understood more readily by reference to the following detailed description of specific aspects of the disclosed subject matter and the Examples and Figures included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an antioxidant" includes mixtures of two or more such antioxidants, reference to "the phytochemical" includes mixtures of two or more such phytochemicals, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt %) of a component, unless specifically stated to the contrary, is based on the total weight of the formulation or composition in which the component is included.

Reference will now be made in detail to specific aspects of the disclosed materials, compounds, compositions, formulations, articles, and methods, examples of which are illustrated in the accompanying Examples and Figures.

Compositions

The oral cavity has been shown to be a location and generator of oxidative stress. However, many individuals exhibit poor oral health patterns and may not be aware of this connection. Oxidative stress in the oral cavity is associated with infection or inflammation of the gums (gingivitis) and other soft tissues (periodontitis), as well as a major contributor to systemic oxidative stress. Disclosed herein are compositions that deliver antioxidants to treat, reduce, or prevent oxidative stress as well as improve oral health.

In some embodiments, the compositions disclosed herein are confectionary compositions. The term "confectionary" as used herein refers to an edible product comprising a sweet component. Confectionary compositions are known in the art and include sugar confectionaries such as hard candy (including, for example, amorphous sugar-glass), toffees, fudges, fondants, jellies, gummies, pastilles, caramels, taffies, nougats, and chewing gums as well as "fat-based confectionary" such as chocolate (including, for example, milk chocolate, dark chocolate, and semi-sweet chocolate), and coatings including, for example, chocolate compound coatings, pastel compound coatings such as white chocolate, and the like.

In some aspects, the confectionary compositions can be chewable. The term "chewable" as used herein, refers to a variety of confectionaries which are chewed in the mouth after oral administration or slowly dissolve after oral administration. In some examples, the chewable confectionary disclosed herein can be retained while chewing in the oral cavity for a period of time greater than one minute, preferably greater than 5 minutes, more preferably greater than 10 minutes. In other examples, the chewable confectionary can be retained while chewing in the oral cavity indefinitely, for example, in the case of a chewing gum.

In specific examples, the chewable confectionary includes a mixture of a sweet component and a gum base portion. Chewable confectionaries provide a means to maintaining efficacious levels of antioxidants in the saliva of a consumer over an extended period of time, such as for at least one minute, at least 5 minutes, or at least 10 minutes. The term "efficacious" refers to means producing or capable of producing a desired effect. When used in respect to an "effective amount" the term refers to the level, amount, serving, or percent that is required to produce or is capable of producing a desired effect.

The chewable confectionary disclosed herein can be in the form of a lozenge, chewing gum, pastille, nougat, toffee, bioadhesive, biodisc, bead, film or tablet that can be chewed, sucked, or adhered to oral tissues, allowing for increased residence time in the oral cavity thereby allowing more complete release and absorption of the antioxidants into the oral and/or buccal cavities. The chewable confectionary can be mounted on a stick in a variety of different shapes. In some examples, the chewable confectionary can be in the form of a chewing gum. Upon release of an efficacious amount of antioxidants from the chewable confectionary into the oral and/or buccal cavities, the chewable confectionary may be expectorated from the mouth, dissolved in the mouth, or swallowed for digestion in the gut.

Antioxidant Active Ingredients

As described herein, the chewable confectionary contains antioxidants for use in reducing oxidative stress in a subject. The antioxidants in the chewable confectionaries can include naturally occurring phenolic compounds, preferably polyphenolic compounds. Naturally occurring phenolic compounds are secondary plant metabolites that possess in common an aromatic ring bearing one or more hydroxyl substituents. Simple phenolic compounds are water soluble and may occur combined with a sugar molecule, as glycosides. However, more complex phenolic compounds, including polyphenolic compounds are generally regarded as lipophilic.

Phenolic compounds are divided into sub-groups including phenols, phenolic acids, phenylpropanoids, flavonoids, flavones, glycoflavones and biflavones, minor flavones, flavonols, flavonones, flavanonals, chacones, anthocyanins, aurones, flavonones, dihydrochalcones, isoflavones, xanthones and stilbenes, hydrolysable and condensed (proanthocyanidins), tannins, and quinines. The chewable confectionaries can include any one or more of the phenolic compounds from the subcategories described herein.

In specific examples, the chewable confectionary can include phenolic compounds selected from 2-hydroxycinnamaldehyde, tannic acid, cinnamic acid, hydroxycinnamatic acids and their esters (e.g. coumaric acids and esters, caffeic acid and their esters, ferulic acid, (iso-) chlorogenic acid, and sinapic acid), carnosic acid, carnosol, carsolic acid, rosmarinic acid, rosmarindiphenol, gentisic acid, ferulic acid, avenanthramide 1 and 2, phytic acid, vanillic acid, gallic acid, protochatechuic acid, p-hydroxybenzaldehyde, p-hydroxybenzoic acid, catechins, epicatechins, flavonoids, phenolic acids or combinations thereof.

The antioxidants present in the chewable confectionary can be derived from a plant material. It is preferred that the chewable confectionary comprises the plant material in its native, unprocessed (naturally occurring/crude) state. The terms "native," "unprocessed" or "naturally occurring" as used herein refer to plant materials comprising antioxidants that are unadulterated and lacking additives and preservatives. The plant material comprising the antioxidant (for example, leaves, root, fruit, bark, or stem of a plant) can be ground to a fine powder, but still having the antioxidant present in a native, unprocessed state. In some embodiments, the unprocessed phytochemical ingredients can be ground plant material having an average particle size 0.1 mm or greater, 0.2 mm or greater, 0.3 mm or greater, 0.4 mm or greater, 0.5 mm or greater, 0.6 mm or greater, 0.7 mm or greater, 0.8 mm or greater, 0.9 mm or greater, 1.0 mm or greater, 1.2 mm or greater, or 1.5 mm or greater. In some embodiments, the unprocessed phytochemical ingredients can be ground plant material having an average particle size of from 0.1 mm to 2.5 mm, from 0.4 mm to 2.5 mm, from 0.5 mm to 2.5 mm, from 0.4 mm to 1.5 mm, from 0.5 mm to 1.5 mm, from 0.4 mm to 1.2 mm, or from 0.6 mm to 1.0 mm. In some examples, the unprocessed phytochemical ingredients can be ground plant material having an average particle size of about 0.8 mm.

The terms "native," "unprocessed" or "naturally occurring" do not encompass a plant extract. the term "extract," also referred to as natural flavor or natural flavoring refers to the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof, whose significant function in food is flavoring rather than nutritional. Extracts include the natural essence or extractives obtained from plants. The extract can be in the form of a solution in a solvent, or the extract can be a concentrate or essence which is free of, or substantially free of solvent. The term extract can be a single extract obtained from a particular extraction step or series of extraction steps or the extract also can be a combination of extracts obtained from separate extraction steps or separate feedstocks. Such combined extracts are thus also encompassed by the term "extract." Without wishing to be bound by theory, it is believed that the concentration of antioxidants such as polyphenols in "plant extracts" is negligible or non-existent due to the filtration of plant particles (ie., spices) to create a homogenous liquid that does not require mixing and does not settle or separate during storage.

As described herein, the chewable confectionary can include a native unprocessed plant material comprising one or more antioxidants. The unprocessed plant material can be selected from the Libiatae family: *Rosimarinus officinalis* (rosemary), *Ocium basilicum* (sweet basil), *Salvia officinalis* (sage), *Origanum valgare* (oregano), *Origanum marjoram* (marjoram), and *Mentha peperita* (mint); the *Laurel* family: *Laurel nobilis* (bay leaves) and *Cinnamomum* sp. (including *Cinnamomum zeylanicum* (cinnamon)); the Umbellifereae family: *Petroselium crispum* (parsley); the Myristicaceae family: *Myristica fragrans* (nutmeg and mace); the Myrtaceae family: *Pimenta dioica* (allspice), *Syzygium aromaticum* (clove); the Lamiacea family: *Hyssopus officinalis* L. Var. *angustifolius* (hyssop); the Lamiaceae family: *Thymus vulgaris* L. (thyme); the Theaceae family: *Camellia sinensis* L. (tea); the Alliaceae family: *Allium sativum* L. (garlic); the Zingiberaceae family: *Zingiber officinale* (ginger) and *Curcuma longa* L. (turmeric); the Rosaceae family: berries.

In specific examples, the chewable confectionary can include a plant material from the genus *Cinnamomum*. The genus *Cinnamomum* contains more than 300 evergreen aromatic trees and shrubs. Four species have great economic importance for their multiple culinary uses as common spices worldwide: Cinnamon zeylanicum Blume (a synonym of Cinnamon verum J. Presl, known as Sri Lanka cinnamon), Cinnamon loureiroi Nees (known as Vietnamese cinnamon), Cinnamon burmanni (Nees & T. Nees) Blume (known as Indonesian cinnamon), and Cinnamon aromaticum Nees (a synonym of Cinnamon cassia (L.) J. Presl, known as Chinese cinnamon). In general, the term cinnamon commonly refers to the dried bark of *C. zeylanicum* and *C. aromaticum* used for the preparation of different types of chocolate, beverages, spicy candies and liquors. Cinnamon bark, leaves, flowers and fruits can be used in the chewable confectionary disclosed herein.

The cinnamon, when present, can be in the chewable confectionary in an amount of 0.1% or greater by weight, based on the weight of the chewable confectionary. For example, cinnamon can be in an amount of 0.2% or greater, 0.3% or greater, 0.4% or greater, 0.5% or greater, 1.0% or greater, 1.5% or greater, 2.0% or greater, 2.5% or greater, 3.0% or greater, 3.5% or greater, 4.0% or greater, 4.5% or greater, 5.0% or greater, 5.5% or greater, 6.0% or greater, 6.5% or greater, 7.0% or greater, 7.5% or greater, 8.0% or greater, 8.5% or greater, 9.0% or greater, 9.5% or greater, or 10% or greater by weight, based on the weight of the chewable confectionary. In some embodiments, cinnamon can be in an amount of 10% or less, 9.5% or less, 8.5% or less, 8.0% or less, 7.5% or less, 7.0% or less, 6.5% or less, 6.0% or less, 5.5% or less, 5.0% or less, 4.5% or less, 4.0% or less, 3.5% or less, 3.0% or less, or 2.5% or less, by weight, based on the weight of the chewable confectionary. In some embodiments, the cinnamon can be in an amount of from 0.1% to 10%, from 0.2% to 8%, from 0.2% to 5%, from 0.5% to 10%, from 0.5% to 5%, or from 0.5% to 3% by weight, based on the weight of the chewable confectionary.

In other specific examples, the chewable confectionary can include a plant material from the species *Myristica fragrans* (nutmeg). Nutmeg's antioxidant activity is attributed to the phytochemicals present naturally (Bamidele et al., 2011). Nutmeg is a tropical fruit native to Banda Island but also cultivated in Penang Island (Weiss, 2002). Skin, pulp, mace and seed are parts of nutmeg which have been widely used as traditional Ayurvedic, Chinese and Thai medicine (Somani et al., 2008). Nutmeg has been shown to possess antioxidant activities, act as good preservative agent and offer benefits in some medical treatments. The major types of total phenolic content found in nutmeg are sabinene, safrole, terpinen4-ol, elemicin, myristicin and myrisfragransin (a lignan). Lignan are the phenolic compounds through the formation of two cinnamic acids. As for total flavonoid content (TFC), it has been found that the seed possesses the highest amount of TFC followed by the skin. The pulp appears to have the lowest TFC while the mace remains the third high in TFC value.

In the family of Myristicaceae species, the abundant flavonoid compounds retrieved were mostly chalcones, flavanones, flavones, dihydroflavanols, flavonols, flavans, flavan-3-ols, virolanes, virolanols, dihydrochalcones, isoflavones and pterocarpans. However, the high TFC found in seed of nutmeg was due to the epicatechin which was also a type of flavonoid, normally found in teas, wine and chocolate. It is among the class of flavan-3-ols with the molecular formula of $C_{15}H_{14}O_6$, which may prevent substances in the bloodstream from oxidizing and clogging the arteries, known as heart-healthy flavonols. Each parts of nutmeg have relatively the same amount of ascorbic acid. Antioxidant properties of fruit are contributed by various phytochemicals, mainly vitamins, carotenoids, terpenoids, alkaloids, flavonoids, lignans, simple phenols and phenolic acids. The high antioxidant activity in nutmeg seed is contributed by caffeic acid and catechin. These two groups are good antioxidants due to their catechol structure which is able to donate hydrogen or electrons to acceptors such as reactive oxygen species or lipid peroxyl radicals easily. Nutmeg's bark, leaves, flowers and fruits can be used in the chewable confectionary disclosed herein.

The nutmeg, when present, in the chewable confectionary can be in an amount of 0.1% or greater by weight, based on the weight of the chewable confectionary. For example, nutmeg can be in an amount of 0.2% or greater, 0.3% or greater, 0.4% or greater, 0.5% or greater, 1.0% or greater, 1.5% or greater, 2.0% or greater, 2.5% or greater, 3.0% or greater, 3.5% or greater, 4.0% or greater, 4.5% or greater, 5.0% or greater, 5.5% or greater, 6.0% or greater, 6.5% or greater, 7.0% or greater, 7.5% or greater, 8.0% or greater, 8.5% or greater, 9.0% or greater, 9.5% or greater, or 10% or greater by weight, based on the weight of the chewable confectionary. In some embodiments, nutmeg can be in an amount of 10% or less, 9.5% or less, 8.5% or less, 8.0% or less, 7.5% or less, 7.0% or less, 6.5% or less, 6.0% or less, 5.5% or less, 5.0% or less, 4.5% or less, 4.0% or less, 3.5% or less, 3.0% or less, or 2.5% or less, by weight, based on the weight of the chewable confectionary. In some embodiments, the nutmeg can be in an amount of from 0.1% to 10%, from 0.2% to 8%, from 0.2% to 5%, from 0.5% to 10%, from 0.5% to 5%, or from 0.5% to 3% by weight, based on the weight of the chewable confectionary. In some embodiments, the weight ratio of cinnamon to nutmeg in the chewable confectionary can be from 1:10 to 10:1, from 1:5 to 5:1, or from 1:2 to 2:1.

In further specific examples, the chewable confectionary can include a plant material from the species *Pimento dioica* (allspice). Allspice has a unique flavor reminiscent of a combination of cinnamon, cloves, ginger, and nutmeg. Allspice can also be obtained from another plant closely related to *P. dioica* called *Pimenta racemose*. Allspice's chemical composition is extremely diverse. Compounds found within however, differ with respect to the plant's part and its geographical origin. For example, allspice is rich in polyphenols and in particular, hydrolysable tannins. The focal phenolic compound within *P. dioica*'s berries is eugenol. Characteristically, *P. dioica*'s berries contain a mixture of phenols, monoterpene hydrocarbons, oxygenated hydrocarbons, sesquiterpene hydrocarbons and oxygenated sesquiterpenes. Extensive amounts of eugenol, methyl eugenol, caryophyllene, β-caryophyllene, limonene, terpinolene, 1,8 cineole, β-selinene, isoeugenol, levophellandrene, α- and β-cubebene, α-copaene, α- and β-gurjunene, α- and β-cadinene, palmitic acid, humulene, terpinene-4-ol, 4,5-cineole, epicatechins, anthocyanidins, eugenol, and gallic acid are found within. Allspice's bark, leaves, flowers and fruits can be used in the chewable confectionary disclosed herein.

The allspice, when present, in the chewable confectionary can be in an amount of 0.1% or greater by weight, based on the weight of the chewable confectionary. For example, allspice can be in an amount of 0.2% or greater, 0.3% or greater, 0.4% or greater, 0.5% or greater, 1.0% or greater, 1.5% or greater, 2.0% or greater, 2.5% or greater, 3.0% or greater, 3.5% or greater, 4.0% or greater, 4.5% or greater, 5.0% or greater, 5.5% or greater, 6.0% or greater, 6.5% or greater, 7.0% or greater, 7.5% or greater, 8.0% or greater, 8.5% or greater, 9.0% or greater, 9.5% or greater, or 10% or greater by weight, based on the weight of the chewable confectionary. In some embodiments, allspice can be in an amount of 10% or less, 9.5% or less, 8.5% or less, 8.0% or less, 7.5% or less, 7.0% or less, 6.5% or less, 6.0% or less, 5.5% or less, 5.0% or less, 4.5% or less, 4.0% or less, 3.5% or less, 3.0% or less, or 2.5% or less, by weight, based on the weight of the chewable confectionary. In some embodiments, the allspice can be in an amount of from 0.1% to 10%, from 0.2% to 8%, from 0.2% to 5%, from 0.5% to 10%, from 0.5% to 5%, or from 0.5% to 3% by weight, based on the weight of the chewable confectionary. In some embodiments, the weight ratio of cinnamon to allspice in the chewable confectionary can be from 1:10 to 10:1, from 1:5 to 5:1, or from 1:2 to 2:1.

Sweetener

The chewable confectionary disclosed herein can include a low- or non-caloric sweetener. As used herein, "low- or non-caloric" means having a reduced number of calories as compared with a full-calorie counterpart, more particularly, "low- or non-caloric" typically means having at least a 50% reduction in calories per serving, e.g., per unit chewable composition. In preferred embodiments, a "low- or non-caloric" chewable composition has a 55% or greater, 60% or greater, 70% or greater, 75% or greater, 80% or greater, 85% or greater, 90% or greater, or 95% or greater reduction in calories per serving. The term "low- or non-caloric" also encompasses "zero-calorie" and "reduced-calorie," therefore, a chewable confectionary may be a reduced caloric composition without being a zero-calorie or low-calorie confectionary.

In some examples, the low- or non-caloric sweetener can include allulose. Allulose (also referred to as D-psicose) is an isomer of fructose, and its sweetness intensity is about 70% of that of sucrose. Allulose is marketed under the tradename of ASTRACEA™, by Tate & Lyle under the tradename of DOLCIA PRIMA™, by AGG under the tradename ALLSWEET™, as well as under the tradename ALLULITE™. ALLULITE™ is a proprietary blend of allulose and fiber in the form of the prebiotic guar gum. Allulose can be added to the chewable confectionary (for example chewing gum) as an amorphous or crystal solid form, or in its liquid form (for example as allulose syrup). Its solubility in water is very high at room temperature, but increases with increased temperature.

In addition to its use as a sweetener in the chewable confectionary, allulose can also be a source of antioxidant, a texture and flavor modifier, a bulking agent, and can improve shelf life properties. For example, allulose has been shown to scavenge reactive oxygen species (ROS), increase expression of antioxidant enzymes, restore the antioxidant glutathione (GSH), and prevent β-cell injury through its antioxidative effects and thus improve glucose tolerance.

The chewable confectionary can include allulose in an amount of 2% or greater by weight, based on the weight of the chewable confectionary. For example, allulose can be present in an amount of 5% or greater, 10% or greater, 15% or greater, 20% or greater, 25% or greater, 30% or greater, 35% or greater, 40% or greater, 45% or greater, or 50% or greater by weight, based on the weight of the chewable confectionary. In some embodiments, allulose can be present in an amount of 90% or less, 85% or less, 80% or less, 75% or less, 70% or less, 65% or less, 60% or less, 55% or less, 50% or less, 45% or less, 40% or less, 35% or less, 30% or less, or 25% or less by weight, based on the weight of the chewable confectionary. In some embodiments, allulose can be present in an amount of from 2% to 90%, from 5% to 80%, from 10% to 75%, from 10% to 60%, from 10% to 50%, or from 20% to 50% by weight, based on the weight of the chewable confectionary. In some embodiments, the weight ratio of cinnamon to allulose in the chewable confectionary can be from 1:5 to 1:50, from 1:5 to 1:30, or from 1:10 to 1:30.

The allulose of the present disclosure can be used in sugar-free (low calorie or calorie-free chewable confectionaries). However, sugar-containing confectionaries are also within the scope of this disclosure. Sugar sweeteners generally include saccharide-containing components commonly known in the chewing gum art which comprise, but are not limited to, sucrose, dextrose, maltose, dextrin, dried invert, sugar, fructose, levulose, galactose, corn syrup solids, tagatose, trehalose, isomaltulose, sugar alcohols, and the like, alone or in any combination. In some instances, sugar alcohols can be used in the chewable confectionary to reduce the sugar and caloric content as well as to provide emulsification of the ingredients into a cohesive texture due to their amphiphilic nature.

Allulose can replace solids like sucrose, dextrose or lactose when used in its powder form, or can replace syrups when used in its liquid or syrup form. At levels of from 0.5% to 25%, allulose can replace part of the solids in the chewable confectionary (such as chewing gum) or, as a liquid, all or part of the syrup in the chewable confectionary. At higher levels of from 20% by weight or greater of the chewable confectionary, allulose can replace all the solid sweetener in the chewable confectionary. Preferably, allulose is the only sweetener in the chewable confectionary and is present in an amount of from 10% to 50%, more preferably from 20% to 40%, of the chewable confectionary.

Unique chewable confectionaries can be obtained when all bulk sweeteners are replaced with allulose. The slightly lower sweetness intensity allows for use of unique flavor combinations. Chewing compositions with allulose can contain a very low amount of moisture in the gum composition, i.e., less than 2%, or may contain a medium amount of moisture, from 2% to 5% by weight, and may even be a soft gum formulation containing 5% moisture or more.

Some sugar-free chewable confectionaries contain high levels of glycerin. Allulose can replace part or all the glycerin used in these types of formulations. Recent advances use hydrogenated starch hydrolysates (HSH) and glycerin preblended and co-evaporated to reduce moisture in some sugar-free chewable confectionaries. Allulose solids and/or syrup can be used to replace part or all the HSH/glycerin blends in the chewable confectionaries. In a similar manner, allulose solids/syrup preblended in glycerin and co-evaporated may be used in the chewable confectionaries. Allulose may be combined with other sugars like dextrose, sucrose, lactose, maltose, invert sugar, fructose and corn syrup solids to form a liquid mix to be blended with glycerin and co-evaporated. Allulose can also be combined with other sugars like tagatose, trehalose, isomaltulose or other carbohydrates such as inulin, bio-agave, isomalt, oligosaccharides, maltodextrins and other types of carbohydrates to form a liquid mix to be blended with glycerin and co-evaporated. Other types of carbohydrates include NUTRIOSE™, ingestible dextrin, fructo-oligosaccharides (FOS) and polydextrose. Allulose solids/syrup can also be mixed with syrup and blended with glycerin and co-evaporated for use in a chewable formulation. Because of allulose's natural humectancy and its low molecular weight, syrup blends with allulose may not need to be co-evaporated with glycerin. Co-evaporated syrup blends of allulose with sugars like dextrose, sucrose, maltose, invert sugar, fructose, tagatose, trehalose, isomaltulose, and other types of carbohydrates as well as combinations of these sugars can be made at high solids and low moisture for chewable confectionaries. In addition, co-evaporated syrups can be made with blends of sorbitol, xylitol, erythritol, maltitol, lactitol, isomalt, mannitol, hydrogenated starch hydrolysates and combinations without glycerin to obtain high solids syrup with low moisture. Other types of low calorie carbohydrates such as inulin indigestible dextrin, and polydextrose may also be used to make co-evaporated syrups.

Gum Base

In addition to the active ingredients, the chewable confectionary can include a water-insoluble chewable gum base portion. The chewable gum base refers to the manufactured or partially manufactured nonnutritive masticatory substance comprised of one or more of the ingredients named and so defined herein. The gum base portion of the chewable confectionary is retained in the mouth throughout the chew. The insoluble gum base can comprise elastomers, resins, fats and oils, waxes, softeners and inorganic fillers. Elastomers may include poly-isobutylene, isobutylene-isoprene copolymer and styrene butadiene rubber, as well as natural latexes such as chicle. Resins can include polyvinyl acetate and terpene resins. Fats and oils can also be included in the gum base, including tallow, hydrogenated and partially hydrogenated vegetable oils, and cocoa butter. Commonly employed waxes include paraffin, microcrystalline and natural waxes such as beeswax and carnauba.

The chewable confectionary can include the gum base in an amount of 5% or greater by weight, based on the weight of the chewable confectionary. For example, gum base can be present in an amount of 7% or greater, 10% or greater, 15% or greater, 20% or greater, 25% or greater, 30% or greater, 35% or greater, 40% or greater, 45% or greater, or 50% or greater by weight, based on the weight of the chewable confectionary. In some embodiments, the gum base can be present in an amount of 95% or less, 90% or less, 85% or less, 80% or less, 75% or less, 70% or less, 65% or less, 60% or less, 55% or less, 50% or less, 45% or less, 40% or less, 35% or less, 30% or less, or 25% or less by weight, based on the weight of the chewable confectionary. In some embodiments, the gum base can be present in an amount of from 5% to 95%, from 5% to 80%, from 5% to 60%, from 10% to 75%, or from 15% to 60% by weight, based on the weight of the chewable confectionary.

The gum base can include filler components. The filler component can be organic or inorganic fillers. In some embodiments, the gum base can include calcium carbonate, magnesium carbonate, talc, as dicalcium phosphate as fillers. The filler can constitute from 5% to 60% or from 5% to 50% by weight of the gum base.

Gum bases can also contain softeners such as glycerol monostearate and glycerol triacetate. Further, gum bases can also contain optional ingredients such as colors and emulsifiers. The present chewable confectionary contemplates employing any commercially acceptable gum base, particularly gum bases that are generally recognized as safe (GRAS), according to the United States Department of Health and Human Services.

Other Ingredients

The chewable confectionaries described herein can further include one or more additional ingredients, including water-soluble and water-insoluble ingredients. The water-soluble portion can dissipate with a portion of the water-insoluble ingredients over a period of time during chewing.

In some aspects, the chewable confectionary can include fat-soluble and water-insoluble vitamins, minerals, softeners, diluents, sweeteners, flavoring agents, colorants, bulking agents, fillers, or combinations thereof. For example, the allulose sweetener can be combined with other sweeteners for use in the chewable confectionary, including but not limited to sucrose, dextrose, fructose, maltose, maltodextrin, xylose, as well as sugar alcohols such as sorbitol, mannitol, xylitol, maltitol, lactitol, and hydrogenated starch hydrolysates such as LYCASIN™. The allulose sweetener can be combined in the chewable confectionary or co-dried or dry blended with the other sweeteners prior to use in the chewable confectionary. Co-drying can be carried out by various methods of spray drying, fluid bed coating, coacervation, and other granulating or agglomerating techniques. Allulose can also be combined with high potency sweeteners including, but not limited to, thaumatin, aspartame, acesulfame K, sodium saccharin, glycyrrhizin, alitame, cyclamate, stevioside, dihydrochalcones, stevia, steviol glycosides, glycosylated steviolglycosides, and luo han guo.

Softeners can be added to the chewable confectionary to optimize the chewability and mouth-feel of the gum. Softeners, also known in the art as plasticizers or plasticizing agents, generally constitute between from 0.1 to 20%, preferably from 0.5 to 20%, more preferably from 1 to 15%, most preferably from 3 to 10%, by weight of the chewable confectionary. Exemplary softeners that can be used in the confectionary compositions disclosed herein can include glycerin, lecithin and combinations thereof. Further, aqueous sweetener solutions such as those containing sorbitol, hydrogenated starch hydrolysates, corn syrup and combinations thereof may be used as softeners and binding agents in chewable confectionaries.

Ingredients for flavoring can include other natural flavoring ingredients that are compatible with sugar for sweetening, such as ginger, cloves, maple sugar (or dehydrated maple syrup), or mixtures thereof, will be finely ground. The flavoring agent can be present in the chewable confectionary in an amount from 0.1% to 10% by weight, preferably from 0.5% to 5% by weight percent of the chewable confectionary. The flavoring agent can comprise essential oils, synthetic flavors, or mixture thereof including, but not limited to, oils derived from plants and fruits such as citrus oils, fruit essences, peppermint oil, spearmint oil, clove oil, oil of wintergreen, anise, and the like. Artificial flavoring components are also contemplated for use in the chewable compositions disclosed herein. Those skilled in the art will recognize that natural and artificial flavoring agents may be combined in any sensory acceptable blend. All such flavors and flavor blends are contemplated by the present disclosure.

Optional ingredients such as colors, emulsifiers and pharmaceutical agents may be added to the chewable compositions.

Method of Making

In general, chewable confectionary can be made by adding the various chewing gum ingredients to a commercially available mixer known in the art. After the ingredients have been thoroughly mixed, the confectionary mass can be discharged from the mixer and shaped into the desired form such as by rolling into sheets and cutting into sticks, extruding into chunks or casting into pellets.

Generally, the ingredients are mixed by first melting the gum base and adding it to the running mixer. The base can also be melted in the mixer itself. Color or emulsifiers can also be added at this time along with the unprocessed phytochemical ingredients to ensure dispersion and homogeneity throughout. A softener such as glycerin may also be added at this time, along with nutritive or non-nutritive syrup and a portion of the bulking agent/sweetener. Further portions of the bulking agent/sweetener can then be added to the mixer. The active ingredients and optionally flavoring agent are typically added with the final portion of the bulking agent. Depending on the sweetness release profile and shelf-stability needed, the allulose sweetener can also be used in combination with coated or uncoated high-potency sweeteners or with high-potency sweeteners coated with other materials and by other techniques. For example, a high-intensity sweetener can be added after the final portion of bulking agent and flavors have been added. Further, the gum formulation can be kneaded or extruded to produce the desired shape and size of individual pieces.

In specific examples, the method of making the chewable confectionary can include mixing a chewable base, one or more unprocessed phytochemical ingredients selected from *Cinnamomum* sp. (cinnamon), *Myristica fragrans* (nutmeg), and *Pimenta dioica* (allspice), and a sweetener comprising allulose.

The entire mixing procedure typically can take from five to fifteen minutes, but longer mixing times may sometimes be required. Those skilled in the art will recognize that many variations of the above described procedure may be followed.

Method of Using

In accordance with this disclosure, the compositions disclosed herein can be used for treating, reducing or preventing oxidative stress in a subject. Methods of using the chewable confectionary to treat, reduce or prevent oxidative stress are therefore disclosed herein. In some embodiments, the method includes a subject consuming a chewable confectionary by placing such composition in the subject's mouth and permitting the subject's natural saliva to dissolve or extract an antioxidant (including hydrophilic and lipophilic antioxidants) contained in the chewable confectionary. A subject can actively masticate (chew) or suck the composition or passively permit the composition to dissolve.

The chewable confectionary can be consumed in a subject's mouth for a period (referred to as the "oral residence time") during which the antioxidant continues to be dissolved or extracted from the chewable confectionary. Typical oral residence times are from 0.5 minute (preferably at least one minute) and may extend up to thirty minutes or more. A typical oral residence time is from 1 to 15 minutes or from 1 to 10 minutes. The preferable method of consuming the chewable confectionaries described herein is by actively chewing the composition. However, the composition can take any physical form suitable for application to an oral surface and provides a therapeutic benefit within or derived from the oral cavity. In various embodiments, the oral composition can be a dentifrice such as a powder, spray or foam; an edible film or a bioadhesive film; a confectionary composition including but not limiting to breath mints, liquid filled beads, low boiled candy, chewing gum, chewy candy, hard boiled candy, coated candy, lozenges, syrups, pressed mints, chocolates and the like. In certain embodiments, the consuming, masticating or adhering of the oral composition is repeated at regular intervals. The preferable chewable confectionary useful in this invention is chewing gum.

The chewable confectionaries disclosed herein include a therapeutically effective amount of antioxidants (from the unprocessed phytochemical ingredients and allulose) to treat, reduce or prevent oral oxidative stress in the subject. In some examples, the chewable confectionary has a phenolic content of at least 100 μg gallic acid equivalents (GAE), such as from 100 μg to 5 mg, from 200 μg to 5 mg, or from 500 μg to 5 mg gallic acid equivalents (GAE) per gram of the unprocessed phytochemical ingredients. In other examples, the chewable confectionary can have an antioxidant capacity of at least 1,500 μM, at least 2,500 μM, at least 3,200 μM, at least 4,000 μM, at least 5,000 μM, at least 10,000 μM, at least 15,000 μM, at least 25,000 μM, at least 50,000 μM, from 1,500 μM to 50,000 μM, from 1,500 μM to 25,000 μM, from 2,500 μM to 20,000 μM, or from 2,500 μM to 10,000 μM Trolox equivalents per 1 gram of the chewable confectionary, as determined by the oxygen radical absorbance (ORAC) assay. In further examples, the subject's saliva can exhibit a total antioxidant capacity depending on the unprocessed plant material used in the formulation. For example, in some cases, the subject's saliva can exhibit a total antioxidant capacity of at least 500 μM, such as from 500 μM to 1,000 μM Trolox equivalents per 1 gram of the chewable confectionary after an oral residence time of greater than one minute, as determined by the oxygen radical absorbance (ORAC) assay. In other examples, the subject's saliva can exhibit an increase in total antioxidant capacity of at least 10%, at least 20%, at least 30%, or at least 50% in Trolox equivalents per 1 gram of the chewable confectionary after an oral residence time of greater than one minute, as determined by the oxygen radical absorbance (ORAC) assay compared to the subject's saliva prior to chewing the chewable confectionary.

The chewable confectionary can be consumed at least once per week, more preferably at least twice per week, most preferably daily. Multiple doses throughout the day can be beneficial than once a day single dosage. The chewable confectionary provided herein allow for three or more servings per day, and can be chewed in the mouth after oral administration, or slowly dissolve after oral administration at least every 60, 90, or 120 minutes. The chewable confectionary can be consumed in the daytime or in the nighttime.

Figure 2:
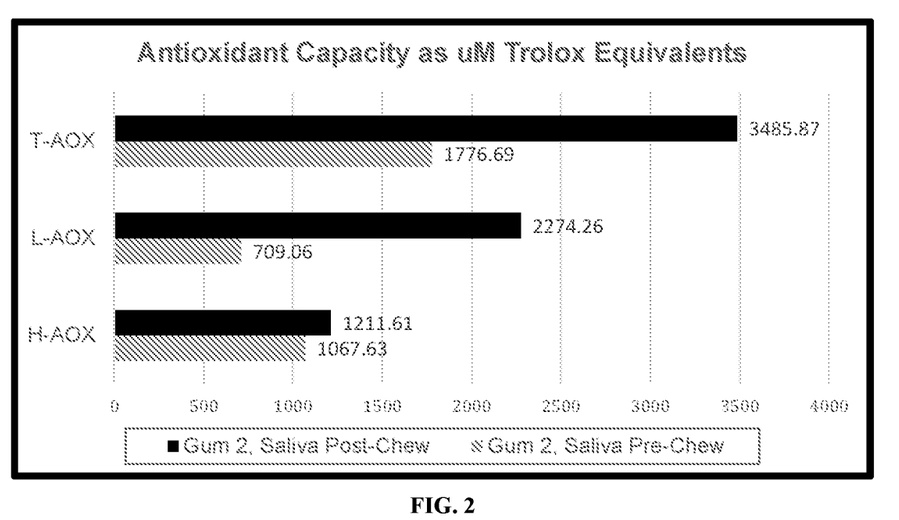
FIG. 2 is a bar graph showing the antioxidant capacity of saliva pre- and post-chewing of gum formulation two (II) containing cinnamon spice.

The chewable confectionary can employ a variety of release mechanisms of the antioxidants, which include delayed, immediate, timed, controlled and variable, alone or in combination using known procedures in the art. In some aspects, because of the lipophilic nature of the plant materials (such as cinnamon), a release mechanism of the antioxidants is not required. FIG. 2 depicts the significant, albeit unexpected, improvements in lipophilic and total antioxidant capacity of saliva upon chewing gum formulation containing cinnamon spice. More specifically, the lipophilic antioxidant capacity of saliva increased 69%. Upon further investigation of these unexpected findings, research has shown that salivary constituents including other antioxidants may enhance the solubility of lipophilic polyphenolic compounds in cinnamon. These findings indicate that the lipophilic polyphenols of cinnamon are liberated in the oral cavity upon chewing the formulated gum despite the hydrophilic nature of saliva.

In other aspects, the chewable confectionaries can utilize the process of encapsulation as a release mechanism for the antioxidants. Some examples of encapsulation procedures include but are not limited to spray drying, fluid-bed coating, spray chilling, coacervation, agglomeration, fixation, absorption, and entrapment alone or in any combination yielding full or partial encapsulation. The plant material comprising the antioxidants can be coated with any of the ingredients as described herein to obtain a coated product yielding improved crunch, sensory properties and/or stability.

In some embodiments, the chewable confectionary can be consumed in combination with an additional therapeutic agent for treating, reducing or preventing oxidative stress.

Kits

The disclosed subject matter also concerns a packaged dosage formulation comprising the chewable confectionaries disclosed herein. A packaged dosage formulation can comprise the chewable confectionary as a chewing gum. For example, the kit can contain one or more, two or more, three or more, four or more, or five or more chewing gums. In some embodiments, the kit can further include directions for use and a suitable number of chewable confectionaries for a time determined for desired efficacy, such as at least two weeks or at least four weeks of consumption. In the context of oxidative stress, a suitable dose(s) is that which will result in treating, reducing, or preventing oxidative stress in a subject. Consuming the chewable confectionary can be at distinct intervals, as can be determined by a person of ordinary skill in the art.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

Example 1: Antioxidant-Infused Gum for Improving Oral Health

Introduction: The connection between oral and vascular oxidative stress and cardiovascular disease is well established. S. T M et al., *Journal of Periodontology* 2013, 84:S24-S29. Thus, a commonly enjoyed oral refreshment, sugar-free chewing gum, has been developed to deliver antioxidants from spices to decrease cardiovascular disease risk by reducing oral oxidative stress and improving oral health. This composition of matter is the first gum-based to deliver antioxidants through inclusion of culinary spices rather than extracts and to impart sweetness by incorporating ALLULITE' as the predominant non-nutritive sweetener rather than polyols. This disclosure documents the antioxidant and polyphenolic content of cinnamon and ALLULITE™ and their ability to be released through this composition of matter culminating in a sugar-free spice-infused gum.

Gum formulation two: the gum formulation was comprised of cinnamon spice and an aqueous-based cinnamon extract (not including any particles or sedimentation). Cinnamon spice was present in the formulation at 1% or greater by weight. Cinnamon extract was also in the formulation at 0.01% by weight.

Figure 1A:
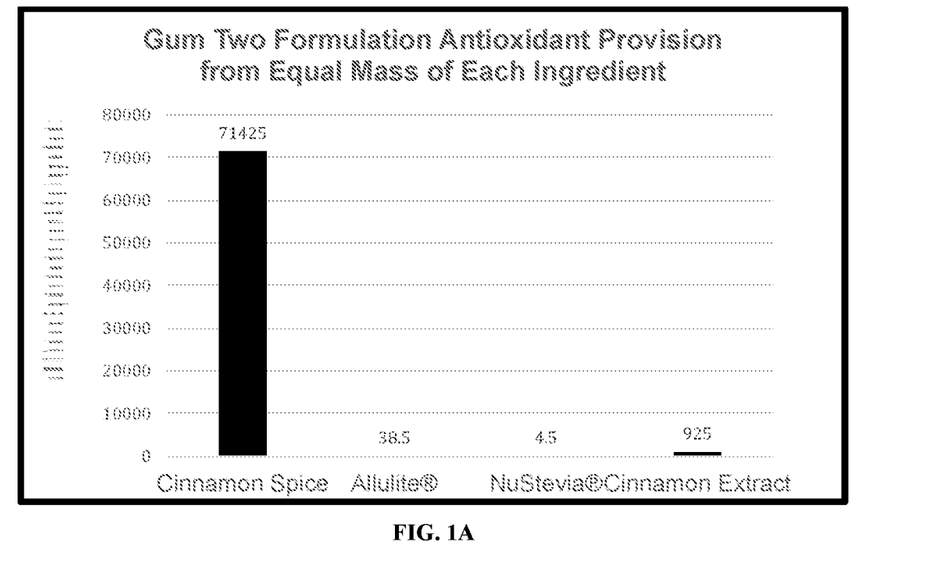
FIGS. 1A-1B are graphs showing the phenolic content (FIG. 1A) and total antioxidant capacity (FIG. 1B) of cinnamon spice and cinnamon extract.
Figure 1B:
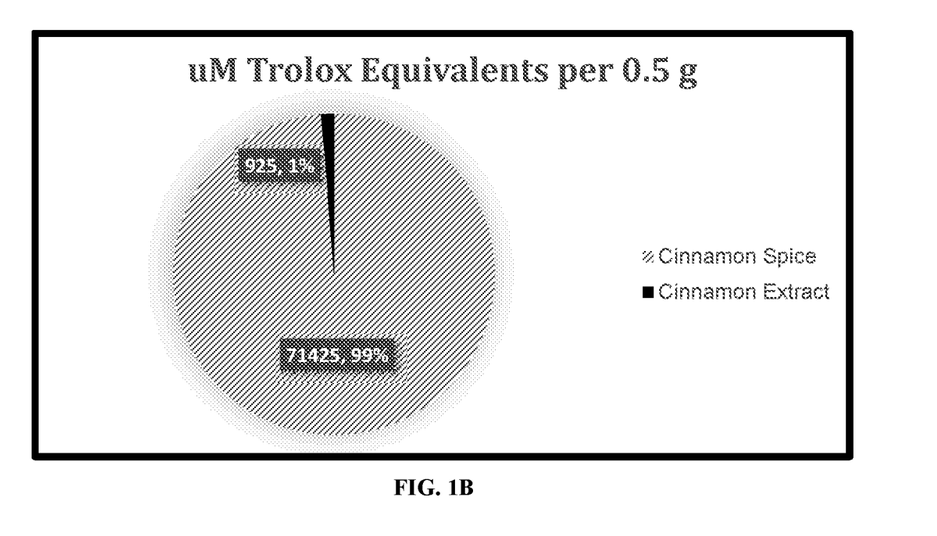

Findings: Cinnamon (*Cinnamomum* species) contains polyphenols with antioxidant functionality including phenolic acids, 2-hydroxycinnamaldehyde, and flavan-3-ols among others. Shan B, ET AL. *Journal of Agricultural and Food Chemistry* 2005, 53:7749-7759. Although polyphenols are abundant in plants and plant-based products, the antioxidant contribution of polyphenols in cinnamon spice exceeds that of most vegetables and some fruits when compared on an equal weight basis. Kyoung C O, et al., *Journal of the Science of Food and Agriculture,* 2005, 85:1715-1724. As such, sugar-free chewing gum formulated to deliver polyphenols from cinnamon spice represents a functional vehicle for delivery of antioxidant compounds that also contribute flavor. Currently, cinnamon-flavored gums on the market use cinnamon extracts/oils. FIGS. 1A and 1B depict the diminished polyphenolic content and subsequent antioxidant activity of the aqueous-based cinnamon extract compared to cinnamon spice on an equal weight basis. Formulations on the market containing cinnamon extract are likely used in place of spices because it has been widely regarded that the lipophilic nature of cinnamon would not allow its dispersal in saliva, a predominantly hydrophilic matrix (~99% water). FIG. 2 depicts the significant and unexpected improvements in lipophilic and total antioxidant capacity of saliva upon chewing gum formulation two containing cinnamon spice. More specifically, the total antioxidant capacity (T-AOX) of saliva increased by 49.1%, the hydrophilic antioxidant capacity (H-AOX) increased by 11.9%, and the lipophilic antioxidant capacity (L-AOX) increased by 68.9%. Upon further investigation of these unexpected findings, research has shown that salivary constituents including other antioxidants may enhance the solubility of lipophilic polyphenolic compounds in cinnamon. Ginsburg I, et al., *Archives of Oral Biology* 2012, 57:1327-1334. Thus, the greatest contributor to the significant increase in total antioxidant capacity upon chewing the formulated gum was derived from the lipophilic polyphenols in cinnamon. These findings indicate that the lipophilic polyphenols of cinnamon are liberated in the oral cavity upon chewing the formulated gum despite the hydrophilic nature of saliva.

Figure 3:
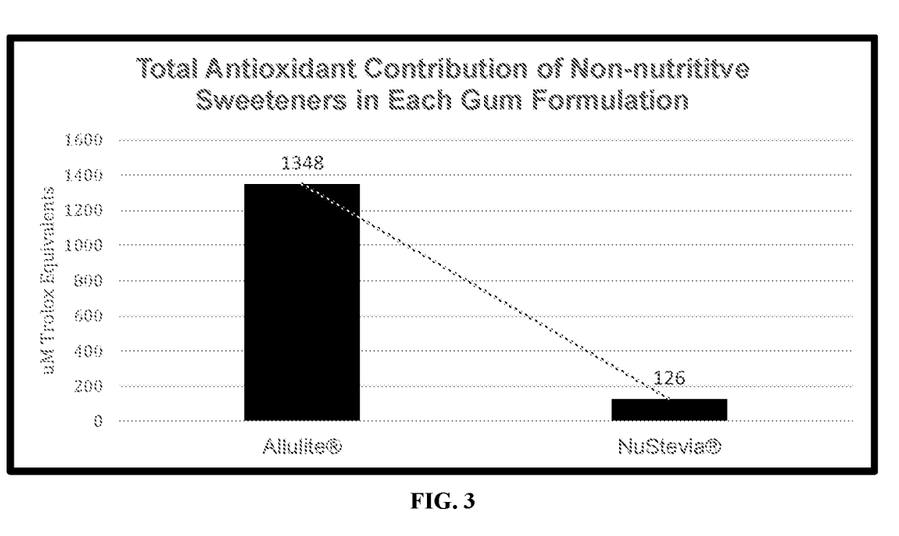
FIG. 3 is a bar graph showing the antioxidant capacity contributed by non-nutritive sweeteners in gum formulation two (II).

ALLULITE™ is a proprietary blend of allulose and fiber in the form of the prebiotic guar gum. D-allulose, C-3 epimer of D-fructose, has 70% of the sweetness of sucrose but almost zero calories and is rarely found in nature. D-allulose is generally recognized as safe (GRAS), according to the United States Department of Agriculture. Allulose may reduce oxidative stress through its antioxidant properties and ability to upregulate endogenous antioxidant compounds. FIG. 3 depicts comparative analysis of the total antioxidant capacity contributed by the non-nutritive sweeteners in gum formulation. To date, there are no sugar-free gum formulations on the market containing allulose or ALLULITE™, but rather the marketed formulations are sweetened primarily with sugar alcohols. Thus, the use of allulose in the form of ALLULITE™ is a new addition to the composition of this functional chewing gum formulated to deliver antioxidants to the oral cavity for reducing oxidative stress.

Methodology:

Antioxidant Capacity. The antioxidant capacity of whole saliva was measured using the oxygen radical absorbance (ORAC) assay in accordance with the method by Prior et al., (*J Agric Food Chem* 2003, 51:3273-3279). The compound 2,2-azobis(2-amidino-propane) dihydrochloride (AAPH) served as the peroxyl radical generator and Trolox, a water-soluble analogue of vitamin E, served as the reference antioxidant standard. The antioxidant capacity of ingredients in gum formulation two were also analyzed by the ORAC method upon extraction in methanol to liberate bound polyphenols.

Total Phenolic Content. Whole saliva and gum formulation ingredients extracted in methanol were analyzed for total polyphenol content according to a modified Folin-Ciocalteu spectrophotometric method. E. H J et al., *Journal of Food Science* 1977, 42:1566-1569 and K Siebert, *Food Quality and Preference* 2003, 15:13-18. Gallic acid served as the reference standard and values are expressed as mg gallic acid equivalents (GAE) per unit.

Figure 4:
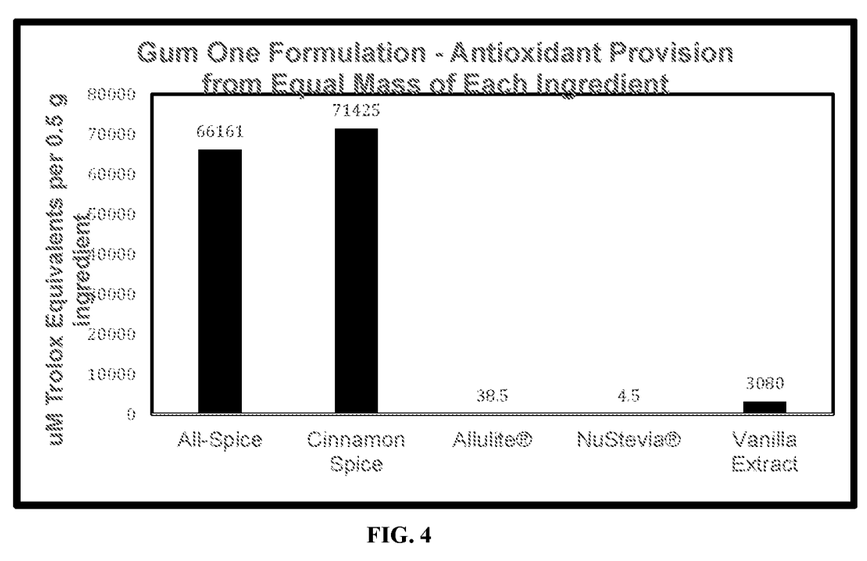
FIG. 4 is a bar graph showing the antioxidant content of each ingredient in a gum formulation (I).

Gum formulation one: a gum formulation comprising apple pie spice (cinnamon, nutmeg, and allspice) in an amount of 1.8% by weight of the formulation and cinnamon spice in an amount of 0.5% by weight of the formulation was prepared. FIG. 4 depicts the antioxidant content of each ingredient in the formulation.

What is claimed is:

1. A chewable confectionary, comprising:
    a chewable base;
    one or more unprocessed plant materials comprising a *Cinnamomum* sp. (cinnamon) dispersed throughout the chewable base, wherein the one or more unprocessed plant materials are grounded particulate materials and present in an amount greater than 0.5% by weight, based on the total weight of the chewable confectionary; and
    a low or non-caloric sweetener comprising allulose,
    wherein a ratio between the cinnamon and allulose is from 1:1 to 1:180; and
    wherein the chewable confectionary has an antioxidant capacity of at least 1,500 µM Trolox equivalents per gram of the chewable confectionary, as determined by the oxygen radical absorbance (ORAC) assay.

2. The chewable confectionary of claim 1, wherein the sweetener consists essentially of allulose.

3. The chewable confectionary of claim 1, wherein the allulose is present in an amount of from 10% to 60% by weight, based on the weight of the chewable confectionary.

4. The chewable confectionary of claim 1, comprising more than one unprocessed plant materials.

5. The chewable confectionary of claim 4, comprising plant materials from *Myristica fragrans* (nutmeg) and *Pimenta dioica* (allspice).

6. The chewable confectionary of claim 1, wherein the unprocessed plant materials comprise cinnamon present in an amount from 0.45% to 10% by weight, based on the weight of the chewable confectionary.

7. The chewable confectionary of claim 5, wherein the plant materials comprise nutmeg present in an amount from 0.45% to 10% by weight, based on the weight of the chewable confectionary.

8. The chewable confectionary of claim 5, wherein the plant materials comprise allspice present in an amount from 0.45% to 10% by weight, based on the weight of the chewable confectionary.

9. The chewable confectionary of claim 1, wherein the unprocessed plant materials have an average particle size from 0.4 mm to 1.5 mm.

10. The chewable confectionary of claim 1, having a polyphenolic content from 100 µg to 5 mg gallic acid equivalents (GAE) per gram of the chewable confectionary.

11. The chewable confectionary of claim 1, further comprising an unprocessed plant material selected from *Rosimarinus officinalis* (rosemary), *Ocium basilicum* (sweet basil), *Salvia officinalis* (sage), *Origanum valgare* (oregano), *Origanum marjorana* (marjoram), and *Mentha peperita* (mint), *Laurel nobilis* (bay leaves), *Petroselium crispum* (parsley), *Syzygium aromaticum* (clove), *Hyssopus officinalis* L. Var. *angustifolius* (hyssop), *Thymus vulgaris* L. (thyme), *Camellia sinensis* L. (tea), *Allium sativum* L. (garlic), *Zingiber officinale* (ginger), *Papaveraceae* spp., *Citrus limon, Citrus sinensis*, or *Curcuma longa* L. (turmeric).

12. The chewable confectionary of claim 1, further comprising a plasticizing agent, bulking agents, diluents, additional sweeteners, colorants, vitamins, probiotics, prebiotics, emulsifiers, flavoring agents, or a combination thereof.

13. The chewable confectionary of claim 1, wherein the chewable confectionary is selected from the group consisting of chewing gums and chewable tablets.

14. A chewing gum comprising the chewable confectionary of claim 1.

15. A method of making a chewable confectionary according to claim 1, comprising mixing a chewable base, one or more unprocessed plant materials comprising a *Cinnamomum* sp. to disperse the plant material throughout the chewable base, and a low or non-caloric sweetener comprising allulose, wherein a ratio between the cinnamon and allulose is from 1:1 to 1:180; and wherein the one or more unprocessed plant materials are grounded particulate materials and present in an amount greater than 0.5% by weight, based on the total weight of the chewable confectionary.

16. A method for treating, reducing or preventing oral oxidative stress in a subject comprising consuming a chewable confectionary according to claim 1, wherein antioxidants in the chewable confectionary are present in a therapeutically effective amount to treat, reduce or prevent oral oxidative stress in a subject.

17. The method of claim 16, wherein the subject's saliva exhibits an increase in total antioxidant capacity of at least 10% in Trolox equivalents per gram of the chewable confectionary after an oral residence time of greater than one minute, as determined by the oxygen radical absorbance (ORAC) assay, compared to the subject's saliva prior to chewing the chewable confectionary.

18. The method of claim 16, wherein the chewable confectionary is consumed at least once per week.

19. The method of claim 16, wherein the chewable confectionary is consumed in combination with an additional therapeutic agent for treating, reducing or preventing oxidative stress.

20. A kit comprising at least three chewable confectionaries according to claim 1.

21. The kit according to claim 20, wherein at least one of the chewable confectionary is a chewing gum.

22. A chewable confectionary, comprising:

a chewable base;

one or more unprocessed plant materials comprising a phytochemical ingredient dispersed throughout the chewable base, wherein the one or more unprocessed plant materials are grounded particulate materials and present in an amount greater than 0.5% by weight, based on the total weight of the chewable confectionary; and a low or non-caloric sweetener comprising allulose, wherein a ratio between the cinnamon and allulose is from 1:1 to 1:180; and wherein the chewable confectionary has an antioxidant capacity of at least 1,500 µM Trolox equivalents per gram of the chewable confectionary, as determined by the oxygen radical absorbance (ORAC) assay.

* * * * *